United States Patent
Lynch et al.

(10) Patent No.: US 7,344,374 B1
(45) Date of Patent: *Mar. 18, 2008

(54) DENTAL OZONE APPARATUS WITH SOURCE OF REDUCTANT SOLUTION

(75) Inventors: Edward Lynch, Northern Ireland (GB); Jurgen H. Schemmer, King (CA); Aylin Baysan, London (GB); Gregory R. Holland, Irvine, CA (US); Tom Weisel, Costa Mesa, CA (US); Roger McPherson, Cerritos, CA (US)

(73) Assignee: Curozone Ireland Ltd., Dublin (IE)

( * ) Notice: Subject to any disclaimer, the term of this patent is extended or adjusted under 35 U.S.C. 154(b) by 0 days.

This patent is subject to a terminal disclaimer.

(21) Appl. No.: 11/393,471

(22) Filed: Mar. 30, 2006

Related U.S. Application Data

(63) Continuation of application No. 10/819,415, filed on Apr. 6, 2004, now Pat. No. 7,021,931, which is a continuation of application No. 10/246,105, filed on Sep. 18, 2002, now Pat. No. 6,743,016, which is a continuation of application No. 09/712,611, filed on Nov. 13, 2000, now Pat. No. 6,454,566.

(51) Int. Cl.
*A61C 17/00* (2006.01)

(52) U.S. Cl. ............................................ 433/80; 433/88

(58) Field of Classification Search ............ 433/80–82, 433/88, 116, 215, 226
See application file for complete search history.

(56) References Cited

U.S. PATENT DOCUMENTS

| 4,021,921 | A | * | 5/1977 | Detaille ..................... 433/81 |
| 4,438,100 | A | * | 3/1984 | Balslev et al. ............. 424/537 |
| 5,928,187 | A | * | 7/1999 | Glukhov et al. ............ 604/23 |

* cited by examiner

*Primary Examiner*—John J Wilson
(74) *Attorney, Agent, or Firm*—Walter A. Hackler

(57) ABSTRACT

Apparatus for the treatment of dental caries includes a source of oxidizing gas and a handpiece for delivering the gas to a tooth. A cup attached to the handpiece is provided for receiving the gas and exposing a selected area of the tooth to the gas. The cup includes a resilient edge for sealably the edge for engaging the tooth around the selected area to prevent escape of a gas therepast.

2 Claims, 3 Drawing Sheets

DENTAL OZONE APPARATUS WITH SOURCE OF REDUCTANT SOLUTION

The present application is a continuation of U.S. Ser. No. 10/819,415 filed Apr. 6, 2004 now U.S. Pat. No. 7,021,931 which is a continuation of U.S. Ser. No. 10/246,105 filed Sep. 18, 2002 now U.S. Pat. No. 6,743,016 which is a continuation of U.S. Ser. No. 09/712,611 filed Nov. 13, 2000 now U.S. Pat. No. 6,454,566.

The present invention generally relates to the treatment of dental caries, and more particularly is directed to apparatus for the treatment of dental caries utilizing an oxidizing gas.

The role of specific micro-organism such as, for example, streptococcus mutants in dental caries is well documented. Enzymes produced by such micro-organisms synthesize dextran from the sucrose passing through the mouth with food or drink resulting in the formation of dental plaque and dental caries.

Dental caries is the decay of teeth caused by demineralization of the enamel surface with organic acids produced by bacteria which adhere to teeth surfaces.

Heretofore, dental caries have been removed through the use of conventional grinding handpieces, lasers and air-blasting apparatus. However high-speed turbine drills or low-speed drills unfortunately will grind both caries and sound dentine. Accordingly, a practitioner must select and grind only caries and consequently, this method depends upon this skill of the practitioner. Lasers have been utilized to remove caries, however, not much success has been achieved for varies reasons. For example, blackened charred tissue blocks the laser radiation which, in turn, prevents the laser from reaching caries therebelow. In addition, heating also interrupts the ablation process.

With regard to air-blasting treatment of caries, sound dentine may also be easily removed, and accordingly, the skill of the practitioner is of outmost importance.

The present invention provides for the treatment of caries without the disadvantages of the prior art hereinabove noted.

SUMMARY OF THE INVENTION

Apparatus for the treatment of dental caries in accordance with the present invention generally includes a source of oxidizing gas and a handpiece for delivering the gas to a tooth. A cup attached to the handpiece, is provided for receiving the gas and exposing a selected area of the tooth to the gas.

The cup may include a resilient edge for sealably engaging the tooth around the selected area to prevent escape of the gas therepast. Alternatively, a suitable sealant may be utilized for providing the sealed engagement between the cup and the tooth. This enables a totally closed system for the application of the gas to the tooth.

A source of oxidizing gas may include an ozone generator and an ozone pump. An aspiration pump may be provided, along with an aspiration line connected to the handpiece, for enabling circulation of the gas into and out of a cup chamber subtending the cup edge. In that regard, a controller may be provided for regulating the ozone and aspiration pumps in order to circulate the gas into an out of the cup chamber at a pressure insufficient to escape past the sealed engagement between and the tooth.

The apparatus may further include a source of reductant, in fluid communication with the cup chamber and a reductant pump may be provided for circulating the reductant through the cup chamber in order to flush the oxidizing gas from the cup chamber and into the aspiration line.

A waste accumulator may be provided and connected to the aspiration line for receiving the reductant. In addition, a filter may be provided for removal of any residual oxidizing gas from the aspiration line.

In one embodiment of the present invention, the cup edge includes a relatively uniform perimeter for sealably engaging a tooth between a cusp and a gingiva. In another embodiment of the present invention, a cup edge may include a contour enabling a sealably engagement with adjacent teeth. More specifically, the cupped edge may have a perimeter contoured for sealably engaging cusps of adjacent teeth.

BRIEF DESCRIPTION OF THE DRAWINGS

The advantages and features of the present invention will be better understood by the following description when considered in conjunction with the accompanying drawings, in which.

DETAILED DESCRIPTION

Figure 1:
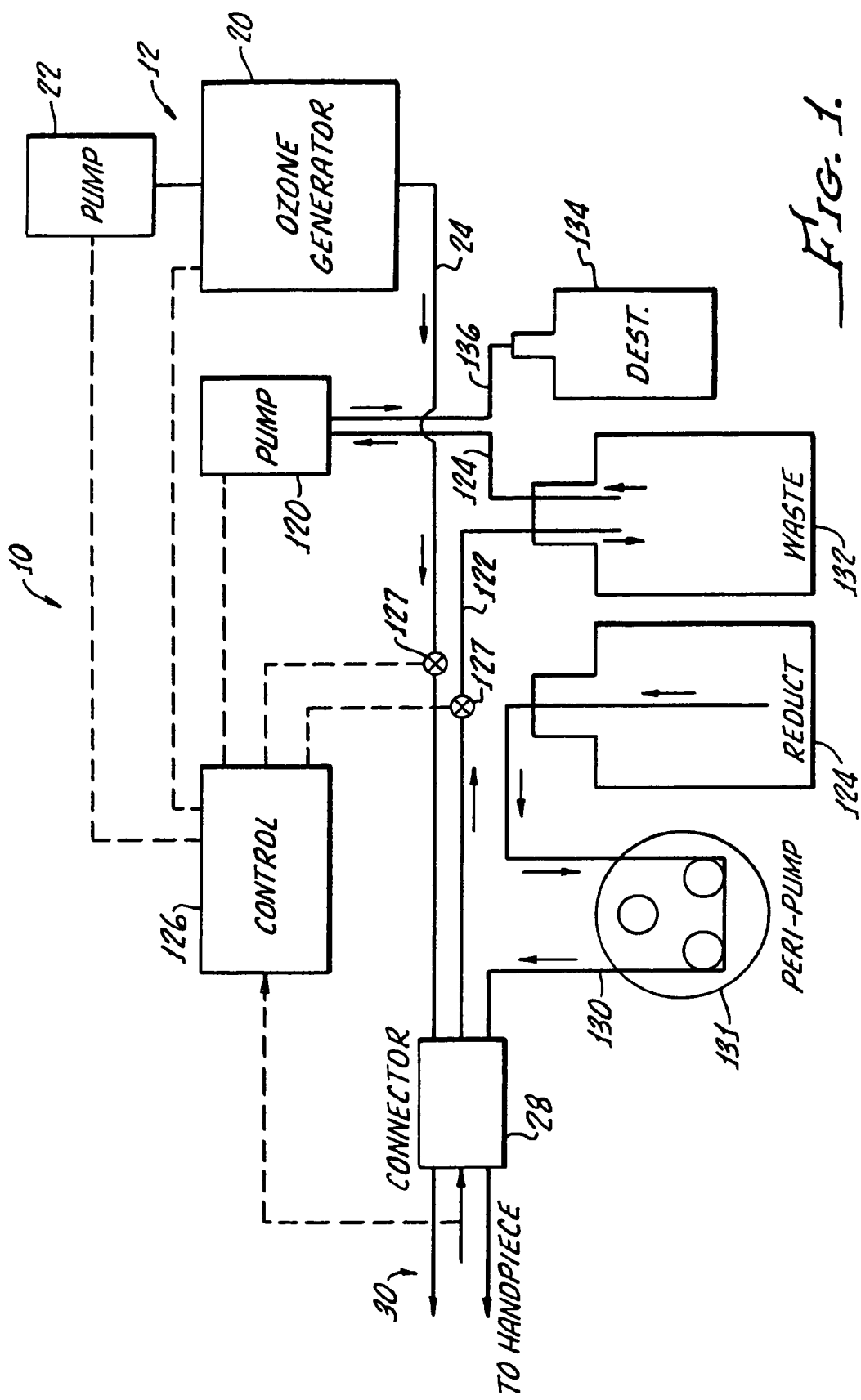
FIG. 1 illustrates a block diagram of apparatus for treatment of dental caries in accordance with the present invention, the apparatus generally includes a source of oxidizing gas, an aspiration pump, a source of reductant, a reductant pump and a controller for providing the oxidizing gas to a handpiece.
Figure 2:
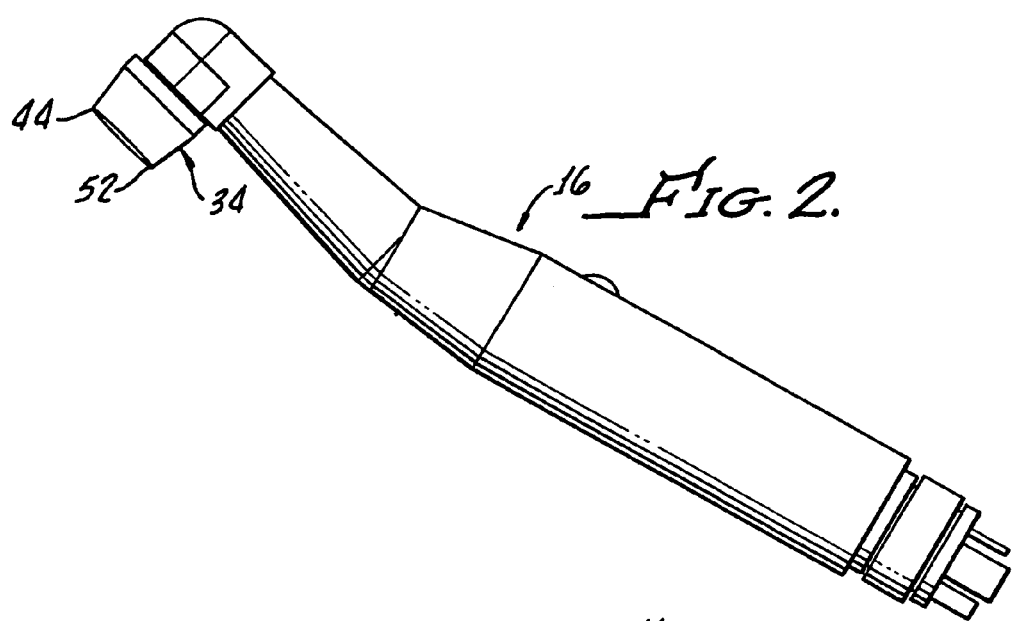
FIG. 2 illustrated a handpiece in accordance with the present invention for delivering a gas to a tooth and generally showing a cup attached to the handpiece for receiving gas.
Figure 3:
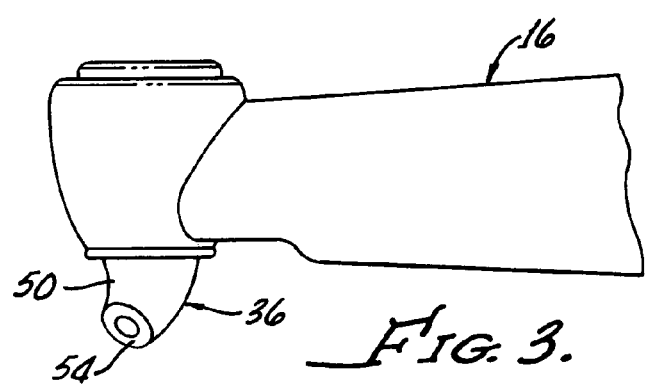
FIG. 3 illustrated the handpiece with an alternative cup embodiment, the alternative embodiment cup having an arcuate shape for facilitating application of oxidizing gas to a tooth.

With reference to FIGS. 1-4, there is shown apparatus 10 in accordance with the present invention for the treatment of dental caries which includes a source 12 of oxidizing gas, preferably ozone, and a handpiece 16 (see FIG. 2) for delivering the gas to a tooth, not shown in FIGS. 1-3. The effectiveness of an oxidizing gas such as ozone is set forth in U.S. Pat. No. 6,409,508 entitled "Use of Ozone For The Preparation of Medicaments For The Treatment of Dental Caries" by Edward Lynch. This patent is incorporated herewith in its entirety including all specification and drawings by this specific reference thereto.

As illustrated in FIG. 1, the ozone source 12 includes an ozone generator 20 and an ozone pump 22 for supplying ozone through a line 24, a connector 28 and lines 30 to the handpiece 16. As used herein, the term "ozone" is intended to embrace any suitable oxidizing gas, pure ozone, ionized air and other ozone gaseous mixtures.

As noted in the referenced international patent application, ozone is delivered at a pressure, concentration and for a period of time sufficient to penetrate the carious tissue and kill substantial all of the micro-organisms within a carious lesion. Specific examples of the use of ozone are set forth in the referenced patent application and are incorporated herewith by the specific reference thereto.

As shown in FIGS. 2-3, cups 34, 36 attached to the handpiece 16 are provided for receiving the gas and exposing a selected area 38 on a tooth 40, see FIG. 3. The cup 34 may be attached to the handpiece 16 in any conventional manner and include a resilient edge, or sidewall, 44 for sealable engaging the tooth 40 to prevent the escape of gas therepast.

Figure 4:
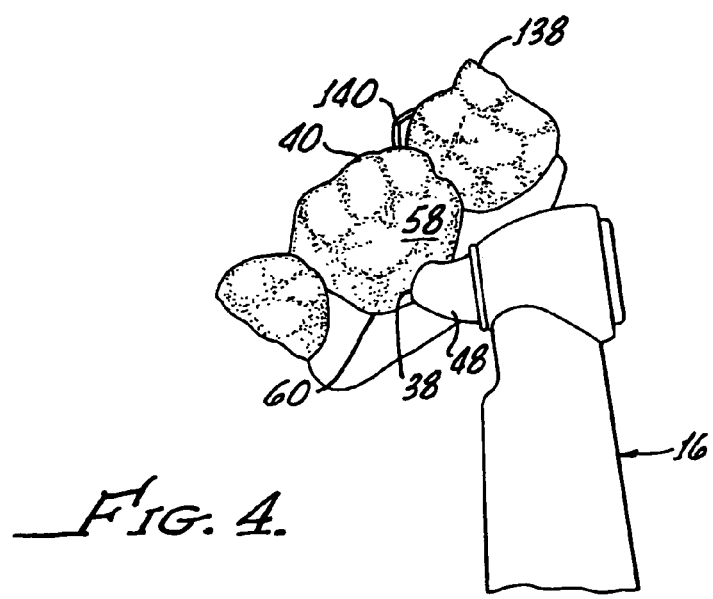
FIG. 4 is a diagram showing application of oxidizing gas to a tooth between a cusp and a gingival utilizing the handpiece and cup shown in FIG. 3.

Many different sized and shaped cups may be utilized, as for example shown in FIG. 3 the cup 36 includes an arcuate trunk 50 to facilitate the placement of the cup 36 over the selected area 38 as shown in FIG. 4. The cups 34, 36 may have relatively uniform perimeters 52, 54 for sealably engaging the tooth 40 between a cusp 58 and a gingiva 60 as shown in FIG. 4.

Figure 6:
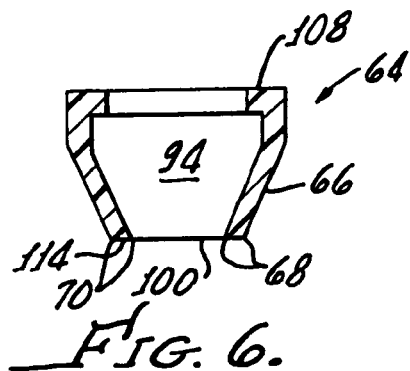
FIG. 6 is a cross sectional view an alternative embodiment of a cup for exposing a selected area of a tooth oxidizing gas.

A further cup embodiment 64 is shown in cross-section in FIG. 6 includes a tapered sidewall 66 that may be used for application of oxidizing gas to a smaller selected area (not shown) on the tooth 40.

While a resilient edge or sidewall may be used to couple the cup to the selected area 38 on the tooth 40, it should be appreciated that a separate sealant 68 (See FIG. 6) may be utilized for providing a sealable engagement between the cup 64 and the tooth 40. In this instance, the sidewall 66 need not be resilient.

Figure 7:
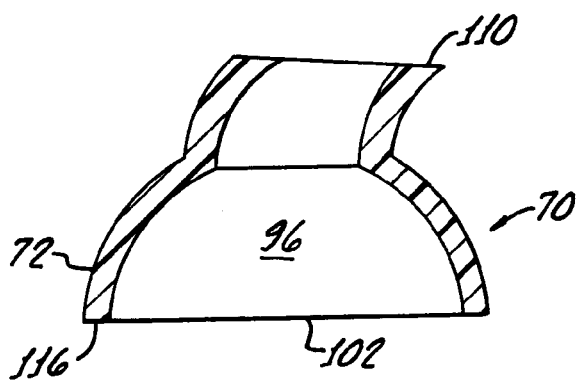
FIG. 7 is a cross sectional diagram showing an alternative embodiment of a cup in accordance with the present invention for exposing adjacent teeth to oxidizing gas.
Figure 8:
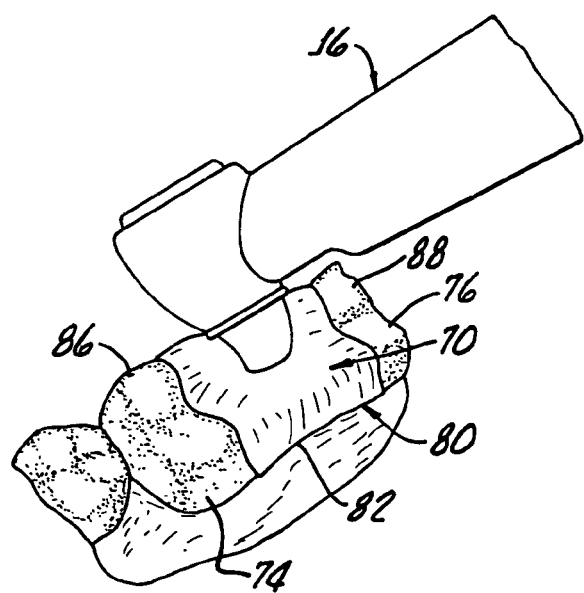
FIG. 8 illustrates the use of the cup shown in FIG. 7 as it may be applied to adjacent teeth.

Another embodiment of a cup 70 is shown in cross-section in FIG. 7 which includes walls 72 which are contoured for enabling the sealable engagement with adjacent teeth 74, 76 as shown in FIG. 8. As shown in FIG. 8, a cup edge 80 has a perimeter contour 82 for providing a sealable engagement with cups 86, 88 of adjacent teeth 74, 76.

Figure 5:
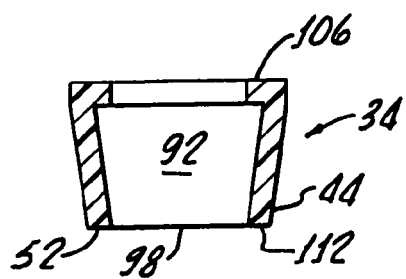
FIG. 5 is cross-sectional view of the cup shown in FIG. 2 that is suitable for use in the present invention.

All of the cups 34, 64, 70, cross-sectionally illustrated in FIGS. 5-7 include cup chambers 92, 94, 96 that subtend cup edges 98, 100, 102. As shown, each of the cups 36, 64, 70 includes walls 44, 66, 72 that define the chambers 92, 94, 96 and include first perimeters 106, 108, 110 for sealably coupling the walls 44, 66, 72 to the handpiece 16. Second perimeters 112, 114, 116 provide for coupling the walls 44, 66, 72 to the tooth 40 and exposing the selected areas 38 to gas circulated in the chambers 92, 94, 96.

As shown in FIG. 6, the embodiment 64 the first perimeter 108 may be larger than the second perimeter 115 or, as shown in FIG. 7, the first perimeter 110 may be smaller than the second perimeter 116. Accordingly, this variation in cup 64, 70 design enables the application of oxidizing gas the any number of tooth contours and to the application of oxidizing gas to a plurality of teeth as hereinabove described.

With reference again to FIG. 1, the apparatus 12 includes an aspiration pump 120 and lines 30, 122, 124 connected to the handpiece 16 for enabling circulation of the ozone into and out of the cup chambers 92, 94, 96.

A controller 126, which may be of any conventional circuit design, is provided for regulating the ozone and aspiration pumps 22, 120 in order to circulate the gas into and out of the cup chambers 92, 94, 96 at a pressure insufficient to permit escape of the gas past a sealed engagement between the cups 34, 64, 70 and teeth 40, 86, 88. Control of the gas flows may also be effected through valves 127, 127 regulated by the controller 126.

Additionally, the apparatus 10 may include a reductant source 128, which is in fluid communication with the cup chambers 92, 94, 96 through lines 30, 130 and a parastatic pump 131. The reductant, which may be a solution of thiocyanate or peppermint, is utilized to flush the cup chambers 92, 94, 96 of oxidizing gas. The oxidizing gas is flushed into the aspiration line 122 following ozone treatment of the tooth 40, 86, 88. The reductant is then aspirated through line 122 and into a waste accumulator 132.

Any residual ozone is then aspirated from the accumulator 132 through the line 124 and into a canister 134 through line 136 for final elimination of the ozone. Thus, the apparatus 12 provides for a totally closed system for the application and removal of ozone to and from teeth 40, 86, 88.

It should also be appreciated that when the cups 34, 36, 64 are utilized between teeth 40, 138 (not shown in FIG. 4) a separate dam 140 may be utilized as necessary to enable cups 34, 36, 64 (not shown in FIG. 4) to sealably enclose a selected area for treatment between the teeth 40, 138.

EXAMPLE 1

Ozone detection (ppm) around the cup using a ozone analyser after either 10 or 20 s of ozone application in vivo Study or Test: Ozone detection (ppm) around the cup 34 using a ozone analyser after either 10 or 20 s of ozone application in vivo Purpose: To assess the maximum ozone detectable level (ppm) around the cup 34 after either 10 s or 20 s of ozone application in vivo.

Study or Test Protocol: 20 primary root carious lesions (PRCLs) were randomly selected when the cross-sectional study was conducted. The tip of the sensor was always held within 2 mm of the edge of the cup, positioned half way between the mesial and occlusal sides of the cup. The maximum ozone detectable level (ppm) around the cup from the extracted teeth using an ozone analyser after 10 s of ozone application. The ozone analyser used was an API 450 model available from ENVIRO Technologys, UK, and was calibrated by the supplier within the previous week of delivery and this device was not used for any other purpose other than this study in the interim.

Overlying plaque was then removed using a hand held standard fine nylon fibre sterile toothbrush with water as a lubricant. Each tooth was dried using dry sterile cotton wool rolls and a dental 3 in 1-air syringe. The excavator blade was used to traverse the lesion in line with long axis of the tooth across the maximum gingival/occlusal dimension. Half of each lesion was removed using a sterile excavator. Subsequently, the remaining lesion was exposed to the ozone gas for a period of either 10 s or 20 s at room temperature (23° C.) and maximum detectable ozone level was also measured using this ozone analyser.

Test Results

The maximum ozone detectable level (ppm) around the cup from lesions for a period of either 10 s (Table 1 and FIG. 1) or 20 s (Table 2 and FIG. 2) ozone application during the treatment of root carious lesions were as follows:

TABLE 1

Maximum ozone detectable level (ppm) after a 10 s of ozone application

| Teeth types | Sites | Ozone detection (10 s) |
| --- | --- | --- |
| Upper left incisor | Mesial | 0.066 |
| Upper right 1. premolar | Buccal | 0.001 |
| Upper right canine | Distal | 0.002 |

TABLE 1-continued

Maximum ozone detectable level (ppm) after a 10 s of ozone application

| Teeth types | Sites | Ozone detection (10 s) |
|---|---|---|
| Upper right 1. molar | Buccal | 0.006 |
| Upper left 2. premolar | Buccal | 0.076 |
| Lower right 2. premolar | Mesial | 0.058 |
| Lower left 1. premolar | Buccal | 0.169 |
| Lower left lateral | Buccal | 0.106 |
| Upper right lateral | Distal | 0.001 |
| Lower left canine | Labial | 0.147 |

TABLE 2

Maximum ozone detectable level (ppm) after a 20 s of ozone application

| Teeth types | Sites | Ozone detection (20 s) |
|---|---|---|
| Lower left lateral | Labial | 0.137 |
| Lower left 1. premolar | Buccal | 0.177 |
| Lower right incisor | Labial | 0.069 |
| Upper right canine | Labial | 0.033 |
| Upper right lateral | Labial | 0.079 |
| Lower left 2. premolar | Buccal | 0.002 |
| Lower right 1. molar | Buccal | 0.083 |
| Upper left lateral | Labial | 0.004 |
| Lower left canine | Labial | 0.056 |
| Upper left 1. premolar | Mesial | 0.001 |

Conclusion: The use of a cup is a safe way of delivering ozone when ozone was applied for a period of either 10 s or 20 s on the root carious lesions.

EXAMPLE 2

Assessment of maximum ozone levels from extracted teeth after the use of ozone for 10 s.—An in vitro test report Study or Test: Assessment of the maximum detectable ozone levels, detected adjacent to the cup, from extracted teeth after the use of ozone for 10 s in vitro.

Purpose: To assess the maximum ozone detectable level (ppm) around a cup from the extracted teeth after a 10 s application of ozone.

1. Study or Test Protocol: 14 extracted teeth were selected. The tip of the sensor was always held within 2 mm of the edge of the cup, positioned half way between the mesial and occlusal sides of the cup. The maximum ozone detectable level (ppm) around the cup from the extracted teeth using an ozone analyser was recorded during 10 s of ozone application with the generator setting on maximum at level 10. The ozone analyser used was the API 450 model and this was calibrated by the supplier within the previous week of delivery. This device was not used for any other purpose other than this study in the interim.

The Ozone Delivery System

After plaque removal with 2 sterile cotton wool rolls, ozone gas was delivered onto the surface of each primary root carious lesion in each extracted tooth for 10 s after the lesion was dried for three seconds with a standard three in one dental syringe.

Test Results:

The maximum ozone detectable level (ppm) around the cup from the extracted teeth after a 10 s application of ozone during the treatment of root carious lesions were as shown in Table 3.

TABLE 3

Maximum ozone detectable level (ppm)

| Teeth types | Sites | Ozone detection |
|---|---|---|
| Upper incisor | Mesial | 0.005 |
| Upper lateral incisor | Labial | 0.004 |
| Upper canine | Labial | 0.003 |
| Upper 1. premolar | Mesial | 0.006 |
| Upper 2. premolar | Distal | 0.002 |
| Upper 1. molar | Buccal | 0.003 |
| Upper 2. molar | Mesial | 0 |
| Lower incisor | Lingual | 0.007 |
| Lower lateral incisor | Distal | 0.001 |
| Lower canine | Mesial | 0 |
| Lower 1. premolar | Distal | 0.009 |
| Lower 2. premolar | Lingual | 0.018 |
| Lower 1. molar | Lingual | 0.016 |
| Lower 2. molar | Mesial | 0.005 |

Conclusion: The use of a cup is a safe way of delivering ozone when ozone was applied for a period of 10 s on the root carious lesions on extracted teeth.

EXAMPLE 3

Measurement of Ozone from the Handpiece

The handpiece 16 from the ozone generator 20 was attached directly to the inlet pipe a Mini-HiCon™ the ozone detector (not shown).

Peak readings from Mini-HiCon™ ($g/Nm^3$)

| Duration (seconds) | Reading 1 ($g/Nm^3$) | Reading 2 ($g/Nm^3$) | Reading 3 ($g/Nm^3$) | Reading 4 ($g/Nm^3$) | Reading 5 ($g/Nm^3$) | Reading 6 ($g/Nm^3$) | Average ($g/Nm^3$) |
|---|---|---|---|---|---|---|---|
| 5 | 5.4 | 5.3 | 5.4 | 4.3 | 5.2 | 5.2 | 5.1 |
| 10 | 4.7 | 4.8 | 4.6 | 3.5 | 4.4 | 4.5 | 4.4 |
| 20 | 4.9 | 5.9 | 6.3 | 6.3 | | | 5.9 |
| 30 | 6.3 | 6.5 | 6.3 | 6.6 | | | 6.4 |
| 60 | 6.6 | 7.0 | 7.0 | 6.7 | | | 6.8 |

Peak readings from Mini-HiCon ™ (ppm)

| Duration (seconds) | Reading 1 (ppm) | Reading 2 (ppm) | Reading 3 (ppm) | Reading 4 (ppm) | Reading 5 (ppm) | Reading 6 (ppm) | Average (ppm) |
|---|---|---|---|---|---|---|---|
| 5 | 2522 | 2475 | 2522 | 2008 | 2428 | 2428 | 2397 |
| 10 | 2195 | 2242 | 2148 | 1635 | 2055 | 2102 | 2063 |
| 20 | 2288 | 2755 | 2942 | 2942 | | | 2732 |
| 30 | 2942 | 3036 | 2942 | 3082 | | | 3000 |
| 60 | 3082 | 3269 | 3269 | 3129 | | | 3187 |

The peak reading was obtained after about 8 seconds (even when the generator was switched on for only 5 seconds) and perhaps represented an "overshoot" before the generator/detector combination stabilized for the >20 second durations. The level then remained fairly constant at between 3.6 and 4.7 g/Nm$^3$.

To Convert from g/m$^3$ to ppm:

The formular weight of ozone is 48 g and therefore 1 g of ozone is 1/48sth of a mole.

The molar volume of an ideal gas (at standard temperature and pressure) is 0.0224138 m$^3$/mol.

$$0.0224138/48 = 467 \times 10^{-6} \, m^3.$$

Therefore 1 g/m$^3$ of ozone in air is 467 ppm. (The ozone detector gives readings as g/Nm$^3$ which is "normalized" to standard temperature and pressure).

Measurement of the Ozone Dissolving in a Potassium Iodide Solution

Ozone was passed through the handpiece 16, immersed in 100 ml of a 20 mM potassium iodide solution in a 250 ml conical flask covered with parafilm for the stated durations. The handpiece was then removed and the flask sealed with a neoprene bung and shaken vigorously. A 1.50 ml aliquot was removed and its electronic absorption spectrum acquired. (These measurements were taken before a diffuser was fitted.) The generator settings were:—air=1, O$_3$=1, vac=0, red=0, regulator-setting=10.

| Duration (seconds) | $\lambda_{max}$ (351 nm) absorbance | $\lambda_{max}$ (351 nm) absorbance | $\lambda_{max}$ (351 nm) absorbance | $\lambda_{max}$ (351 nm) average absorbance |
|---|---|---|---|---|
| 1 | 0.06 | 0.08 | 0.11 | 0.08 |
| 2 | 0.50 | 0.44 | 0.26 | 0.40 |
| 3 | 0.70 | 0.56 | 0.42 | 0.56 |
| 4 | 0.77 | 0.69 | 0.50 | 0.65 |
| 5 | 0.90 | 0.84 | 0.51 | 0.75 |
| 6 | 1.08 | 0.99 | 0.68 | 0.92 |
| 7 | 1.17 | 1.11 | 0.75 | 1.01 |
| 8 | 1.30 | 1.27 | 0.95 | 1.17 |
| 9 | 1.40 | 1.40 | 1.19 | 1.33 |
| 10 | 1.57 | 1.43 | 1.38 | 1.46 |

To Calculate the Concentration from the Peak Absorbance:

$$A = E \times C \times L$$

where

L=cell path length (1 cm)
C=concentration (mol)
E=extinction coefficient
A=absorbance
E for 1M=2.97×10$^4$
E for 1 μM=0.0297
C=A÷E⇒ concentration in μmol/l is absorbance/0.0297

| Duration (seconds) | $\lambda_{max}$ absorbance (average of 3) | Concentration (μmol/l) | Total dissolved ozone (μmol) | Ozone (μg) | Volume of air/ozone mixture (ml) | Ozone in air (μg/ml = g/m$^3$) | Ozone in air (ppm) |
|---|---|---|---|---|---|---|---|
| 1 | 0.08 | 2.69 | 0.269 | 13 | 8 | 1.625 | 759 |
| 2 | 0.40 | 13.47 | 1.347 | 65 | 16 | 4.063 | 1897 |
| 3 | 0.50 | 18.86 | 1.886 | 91 | 24 | 3.792 | 1771 |
| 4 | 0.65 | 21.89 | 2.189 | 105 | 32 | 3.281 | 1532 |
| 5 | 0.75 | 25.25 | 2.525 | 121 | 40 | 3.025 | 1413 |
| 6 | 0.92 | 30.98 | 3.098 | 149 | 48 | 3.104 | 1450 |
| 7 | 1.01 | 34.39 | 3.439 | 165 | 56 | 2.946 | 1376 |
| 8 | 1.17 | 39.39 | 3.939 | 189 | 64 | 2.953 | 1379 |
| 9 | 1.33 | 44.79 | 4.479 | 215 | 72 | 2.986 | 1394 |
| 10 | 1.46 | 49.16 | 4.916 | 236 | 80 | 2.950 | 1378 |

NMR Analysis of Plaque/caries

1. Plaque samples were obtained from volunteers and each sample was divided into two. Half of each sample was treated with ozone and half left untreated as a control.

2. The samples were each weighed. Then 600 μl of 0.5 M $HClO_4$ was added to each sample and rotamixed.

3. The samples were centrifuged and supernatants retained.

4. The samples were neutralized to a pH of between 6 and 8 and the volume of KOH used was noted.

5. The samples were centrifuged again and 600 μl of supernatant were taken for analysis.

6. 70 μl of $D_2O$ and 30 μl of sodium 3-trimethylsilyl-(2, 2,3,3,-$^2H_4$)-propionate (5 mM in $D_2O$) were added prior to NMR analysis.

NMR Analysis of Saliva

1. Saliva samples were obtained from volunteers and each sample was divided into two. Half of each sample was treated with ozone and half left untreated as a control.

2. The samples were centrifuged and supernatants retained.

3. 70 μl of $D_2O$ and 30 μl of sodium 3-trimethylsilyl-(2, 2,3,3,-$^2H_4$)-propionate (5 mM in $D_2O$) were added prior to NMR analysis.

| Iodine Standards (in 20 mM potassium iodide) | |
| --- | --- |
| Iodine Concentration | Absorbance at 351 nm |
| 4 uM | 0.1144 |
| 5 uM | 0.1410 |
| 7 uM | 0.1690 |
| 10 uM | 0.2002 |

Although there has been hereinabove described apparatus for the treatment of dental caries in accordance with the present invention for the purpose of illustrating the manner in which the invention may be used to advantage, it will be appreciated that the invention is not limited thereto. Accordingly, any and all modifications, variations or equivalent arrangements which may occur to those skilled in the art, should be considered to be within the scope of the invention as defined in the appended claims.

What is claimed is:

1. Dental apparatus comprising:
a source of ozone gas;
a handpiece for delivering the gas to a tooth;
a cup attached to said handpiece for receiving the gas, said cup including means for directing the gas onto a selected area of the tooth;
a source of reductant solution in fluid communication with the cup;
means for enabling circulation of the gas into and out of the cup for a period of time sufficient to penetrate tissue and kill substantially all of the micro-organisms within a carious lesion;
a reductant pump for circulating the reductant solution through the cup and into said aspiration line; and
a waste accumulator connected to said aspiration line for receiving the reductant solution.

2. Dental apparatus comprising:
a source of ozone gas;
a handpiece for delivering the gas to a tooth;
a cup attached to said handpiece for receiving the gas, said cup including means for directing the gas onto a selected area of the tooth;
a source of reductant solution in fluid communication with the cup;
means for enabling circulation of the gas into and out of the cup for a period of time sufficient to penetrate tissue and kill substantially all of the micro-organisms within a carious lesion;
a reductant pump for circulating the reductant solution through the cup and into said aspiration line;
a waste accumulator connected to said aspiration line for receiving the reductant solution; and
a filter for removal of any residual oxidizing gas from the aspiration line.

* * * * *